US008630811B2

(12) United States Patent
Anderson et al.

(10) Patent No.: US 8,630,811 B2
(45) Date of Patent: Jan. 14, 2014

(54) METHOD FOR COMBINING INDIVIDUAL RISK VARIABLES DERIVED FROM CARDIOPULMONARY EXERCISE TESTING INTO A SINGLE VARIABLE

(75) Inventors: Stephen T. Anderson, North Oaks, MN (US); Dean J. MacCarter, Englewood, CO (US); Bruce D. Johnson, Rochester, MN (US)

(73) Assignee: Shape Medical Systems, Inc., St. Paul, MN (US)

( * ) Notice: Subject to any disclaimer, the term of this patent is extended or adjusted under 35 U.S.C. 154(b) by 0 days.

(21) Appl. No.: 13/533,519

(22) Filed: Jun. 26, 2012

(65) Prior Publication Data

US 2012/0265447 A1    Oct. 18, 2012

Related U.S. Application Data

(63) Continuation-in-part of application No. 12/209,376, filed on Sep. 12, 2008, now abandoned.

(60) Provisional application No. 60/993,998, filed on Sep. 17, 2007.

(51) Int. Cl.
*G06F 19/00* (2011.01)
*A61B 5/08* (2006.01)

(52) U.S. Cl.
USPC ............................................. 702/19; 600/529

(58) Field of Classification Search
None
See application file for complete search history.

(56) References Cited

U.S. PATENT DOCUMENTS

| 4,930,519 | A | 6/1990 | Anderson et al. |
| 2003/0208106 | A1 | 11/2003 | Anderson et al. |
| 2004/0138716 | A1 | 7/2004 | Kon et al. |
| 2004/0260185 | A1 | 12/2004 | Anderson et al. |
| 2009/0281415 | A1* | 11/2009 | Cupps et al. .................. 600/410 |

OTHER PUBLICATIONS

Aaronson et al. Development and Prospective Validation of a Clinical Index to Predict Survival in Ambulatory Patients Referred for Cardiac Transplant Evaluation. Circulation vol. 95, pp. 2660-2667 (1997).*
Woods et al. A Pulmonary Hypertension Gs Exchange Severity (PH-GXS) Score to Assist With the Assessment and Monitoring of Pulmonary Arterial Hypertension. American Journal of Cardiology vol. 109, pp. 1066-1072 (Apr. 1, 2012).*
Woods et al. 2011 The usefulness of submaximal exercise gas exchange to define pulmonary arterial hypertension Journal of Heart and lung Transplantation vol. 30, pp. 1133-1142 (Oct. 1, 2011).*

(Continued)

*Primary Examiner* — John S Brusca
(74) *Attorney, Agent, or Firm* — Nikolai & Mersereau, P.A.; C. G. Mersereau

(57) ABSTRACT

A method of pattern recognition for classifying the functional status of patients with chronic disease comprising characterizing the functional status based on a multivariable index (MVI) scoring system wherein the MVI is computed by summing a plurality of individual variable values as individual variable indexes (IVI) and dividing the sum by the number of variables and wherein the plurality of IVI includes rest $PetCO_2$, $\Delta PetCO_2$, $SaO_2$, QUES, $V_e/VCO_2$ slope and $P_{cap}$ and wherein each IVI is given an equivalent value of <1.00 to >=4.00, the number increasing with increasing severity yielding an MVI value ranging from <1.00 to >=4.00, normal to severe-very severe.

18 Claims, 16 Drawing Sheets

(56) References Cited

OTHER PUBLICATIONS

Woods et al. 2012 A Pulmonary Hypertension Gas Exchange Severity (PH-GXS) Score to Assist With the Assessment and Monitoring of Pulmonary Arterial Hypertension American Journal of Cardiology vol. 109, pp. 1066-1072 (Apr. 1, 2012).*

Dresing et al, American Journal of Cardiology, *Usefulness of Impaired Chronotropic Response to Exercise as a Predictor of Mortality, Independent of the severity of Coronary Artery Disease*, vol. 86, Sep. 15, 2000, pp. 602-609.

Robbins et al, Circulation *Ventilatory and Heart Rate Response to Exercise: Better Predictors of Heart Failure Mortality Than Peak Oxygen Consumption*, vol. 100, 1999, pp. 2411-2417.

Vivekananthan et al, Journal of the American College of Cardiology, *Heart Rate Recovery After Exercise is a Predictor of Mortality, Independent of the Angiographic Severity of Coronary Disease*, vol. 42, No. 5, 2003, pp. 831-838.

Watanabe et al, Circulation *Heart Rate Recovery Immediately After Treadmill Exercise and Left Ventricular Systolic Dysfunction as Predictors of Mortality: The Case of stress Echocardiography*, vol. 104, 2001, pp. 1911-1916.

Arena et al, Journal of Cardiac Failure, *The Minute Ventilation/Carbon Dioxide Production Slope is Prognostically Superior to the Oxygen Uptake Efficiency Slope*, vol. 13, No. 6, 2007, pp. 462-469.

Davies et al, European Heart Journal, *Enhanced Prognostic Value From Cardiopulmonary Exercise Testing in Chronic Heart Failure by Non-Linear Analysis: Oxygen Uptake Efficiency Slope*, vol. 27, 2006, pp. 684-690.

Hollenberg et al, Journal of American College of Cardiology, *Oxygen Uptake Efficiency Slope: An Index of Exercise Performance and Cardiopulmonary Reserve Requiring Only Submaximal Exercise*, vol. 36, No. 1, 2000, pp. 194-201.

Arena et al, Chest, *Influence of Heart Failure Etiology on the Prognostic Value of Peak Oxygen Consumption and Minute Ventilation/Carbon Dioxide Production Slope*, vol. 128, 2005, pp. 2812-2817.

Corra et al, American Heart Journal, *Ventilatory Response to Exercise Improves Risk Stratification in Patients with Chronic Heart Failure and Intermediate Functional Capacity*, vol. 143, 2002, pp. 418-426.

Guazzi et al, American Heart Journal, *Exercise Oscillatory Breathing and Increased Ventilation to Carbon Dioxide Production Slope in Heart Failure: An Unfavorable Combination with High Prognostic Value*, vol. 153, 2007, pp. 859-867.

Kleber et al, Circulation *Impairment of Ventilatory Efficiency in Heart Failure: Prognostic Impact*, vol. 101, 2000, pp. 2803-2809.

Ponikowski et al, Circulation, *Enhanced Ventilatory Response to Exercise in Patients With Chronic Heart Failure and Preserved Exercise Tolerance: Marker of Abnormal Cardiorespiratory Reflex Control and Predictor of Poor Prognosis*, vol. 103, 2001, pp. 967-972.

Arena et al, Circulation,, *Development of a Ventilatory Classification System in Patients with Heart Failure*, vol. 115, 2007, pp. 2410-2417.

McRae III et al, Journal of American College Cardiology, *The Oxygen Uptake Efficiency Slope as a Predictor of Mortality in Chronic Heart Failure*, vol. 43, 2002, abstract 856-3 p. 183A.

Hansen et al, Chest, *Mixed-Expired and End-Tidal $CO_2$ Distinguish Between Ventilation and Perfusion Defects During Exercise Testing in Patients with Lung and Heart Diseases*, vol. 132, 2007, pp. 977-983.

* cited by examiner

| Patient : Table | | | | | | | | |
|---|---|---|---|---|---|---|---|---|
| P_Key | FirstName | LastName | Age | Height | Weight | Sex | DOB | Address |
| 13 | Steve | Anderson | 60 | 72 | 200 | Male | 3/8/1947 | |

| Key | TypeTest | Today | Protocol | PacerPre | PacerPost | WebSiteRecieve | TI | |
|---|---|---|---|---|---|---|---|---|
| 315 | Step (Submax) | 3/12/2007 8:46:00 AM | | | | ☐ | | |

| Key | Phase | Breath Count | PetCO2 | VCO2 | VO2 | VT | HeartRate | RR |
|---|---|---|---|---|---|---|---|---|
| 386 | Rest | 26;27;27;27;27; | 33.7;33.8;33.8; | 18;16.2;16.2;16 | 19.7;18.1;18.1; | 859.3;715.7;71 | 72;73;73;73;73; | 19.1;23.1;23 |
| 387 | Exercise | 57;57;57;58;58; | 34.5;34.5;34.5; | 15.3;15.3;15.3; | 18.3;18.3;18.3; | 661.1;661.1;66 | 75;75;75;76;76; | 18.7;18.7;18 |
| 388 | Recovery | 110;110;111;11 | 39.3;39.3;38.1; | 42.6;42.6;41.1; | 51.1;51.1;47.9; | 1364.4;1364.4;1 | 94;94;94;94;94; | 20.5;20.5;22 |
| (AutoNumber) | | | | | | | | |

| 316 | CRT Optimization | 3/12/2007 8:54:00 AM | | | | | | |
| 317 | Step (Submax) | 3/12/2007 9:09:00 AM | | | | | | |

Figure 3

| Data pairs used to compute slope | Normal Value (NV) | Cutoff Point (COP) |
|---|---|---|
| VE/VCO2 | 26.1 | 35 |
| VO2/log VE | 2.12 | 1.39 |
| % heart rate reserve/% metabolic reserve | 0.94 | 0.51 |
| HR/time | 28 | 12 |
| Data pairs used to compute delta | | |
| delta PetCO2 | 1.8 | 1 |

Figure 4

For ventilation efficiency, RPve = 1 + ((NV – measured value)/(COP-NV))
NV=26.1, COP=35.0

For O2 Uptake efficiency, RPo2es = 1+ ((measured value – NV)/(NV-COP))
NV=2.12, COP=1.39

For HR recovery, RPhrr = 1+ ((measured value – NV)/ )/(NV-COP))
NV=28, COP=12

For CRI, RPcri = 1+ ((measured value – NV)/ )/(NV-COP))
NV=.94, COP=.51

For delta PetCO2, RPpetco2 = 1+ ((measured value – NV)/ )/(NV-COP))
NV=1.8, COP =1.0

Figure 7

Figure 10a and 10b. MVI score sorted and plotted for each subject for PH and HF populations showing the score to be a continuous variable.
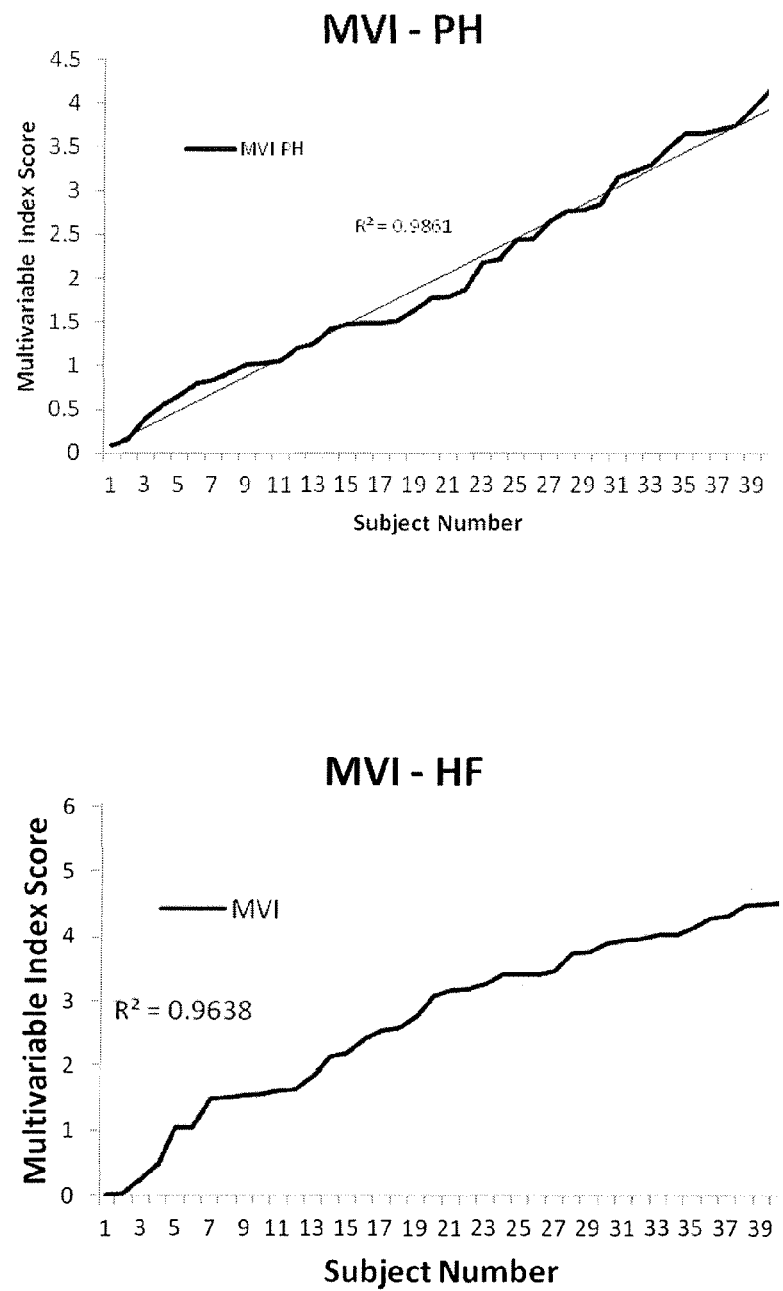

Figure 11a and 11b. WHO classification for PH group and NYHA classification for HF group
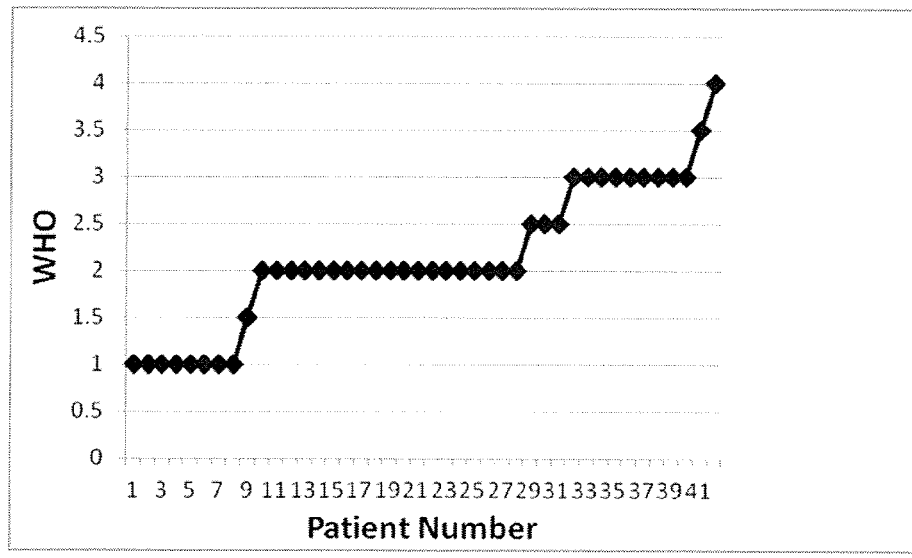
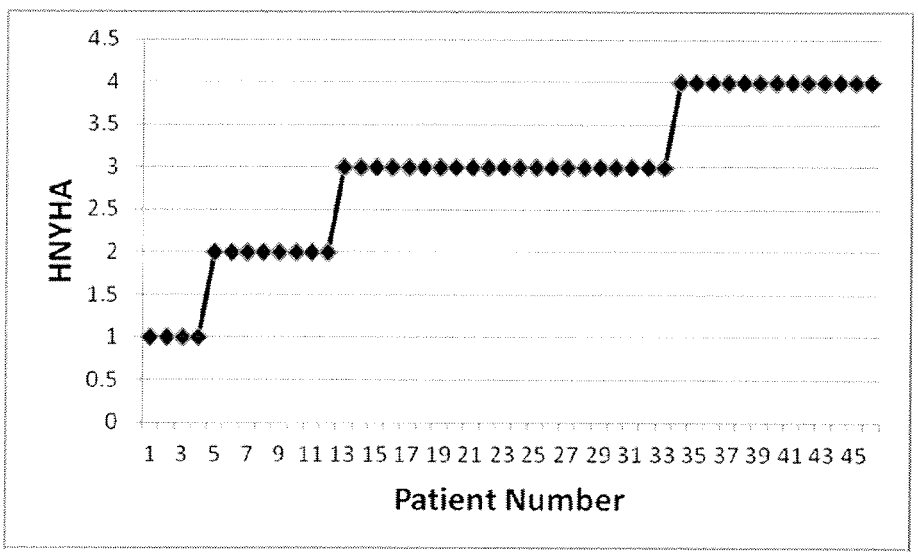

Figure 12. Final Model with examples of *HF patients* according to gas exchange severity.
|  | Severe – Very Severe | Moderate – Severe | Mild – Moderate | Normal – Mild | Normal |
|---|---|---|---|---|---|
| Age (yr) | 48 | 50 | 52 | 46 | 58 |
| Weight (kg) | 79 | 66 | 82 | 74 | 72 |
| BNP | 2100 | 829 | 617 | 327 |  |
| Rest PetCO$_2$ | 28.4 | 31.5 | 41.3 | 34.2 | 29.2 |
| Delta PetCO$_2$ | -5.5 | -0.7 | -4.1 | -0.8 | 5.1 |
| SaO$_2$ | 94 | 97 | 95 | 91 | 95 |
| OUES | 0.8 | 0.7 | 1.1 | 1.5 | 2.1 |
| V$_E$/VCO$_2$ slope | 56.5 | 35.5 | 36.0 | 35.1 | 29.9 |
| PAP capacitance | 135 | 159 | 274 | 362 | 388 |
| Cum MPI 6 | 21.58 | 14.38 | 10.54 | 2.23 | -0.13 |
| / by 6 | 3.60 | 2.40 | 1.76 | 0.37 | -0.02 |
| Cum MPI 7 | 28.20 | 20.42 | 13.69 | 7.44 | 0.17 |
| / by 7 | 4.03 | 2.92 | 1.96 | 1.06 | 0.02 |
| Modifier | 0.5 | 0.25 | 0.25 | 0 | 0 |
| MVI | 4.03 | 3.17 | 2.21 | 1.06 | 0.02 |
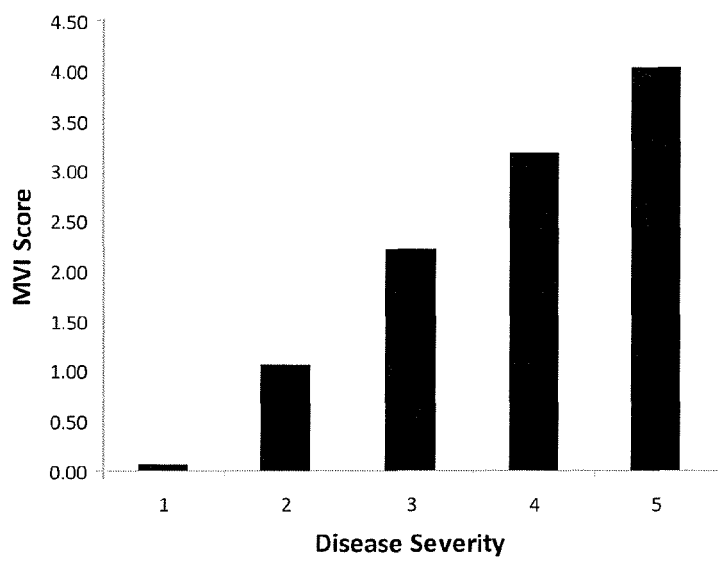

Figure 13. Final Model with examples of *PH patients* according to gas exchange severity.
|  | Severe - Very Severe | Moderate - Severe | Mild - Moderate | Normal - Mild | Normal |
|---|---|---|---|---|---|
| Age | 53 | 44 | 57 | 41 | 52 |
| Weight | 76 | 66 | 73 | 68 | 77 |
| NT pro BNP | 3056 | 918 | 518 | 103 |  |
| Rest PetCO$_2$ | 29.1 | 34.9 | 30.2 | 37.3 | 34.2 |
| Delta PetCO$_2$ | -7.3 | -1.8 | 2.2 | -0.8 | 3.7 |
| SaO$_2$ | 90 | 93 | 91 | 91 | 95 |
| OUES | 1.15 | 0.78 | 1.08 | 1.53 | 1.71 |
| V$_E$/VCO$_2$ slope | 61.0 | 36.2 | 33.7 | 35.1 | 29.4 |
| PAP capacitance | 166 | 242 | 226 | 362 | 396 |
| Cum MPI 6 | 21.9 | 13.0 | 11.2 | 6.2 | 1.0 |
| / by 6 | 3.7 | 2.2 | 1.9 | 1.0 | 0.2 |
| Cum MPI 7 | 27.7 | 17.0 | 15.5 | 7.1 | 1.1 |
| / by 7 | 4.0 | 2.4 | 2.2 | 1.0 | 0.2 |
| MVI PetCO$_2$ | -14.4 | -5.16 | n/a | 1.14 | n/a |
| Modifier | 1 | 0.75 | 0 | 0 | 0 |
| MVI | 4.96 | 3.18 | 2.22 | 1.02 | 0.15 |
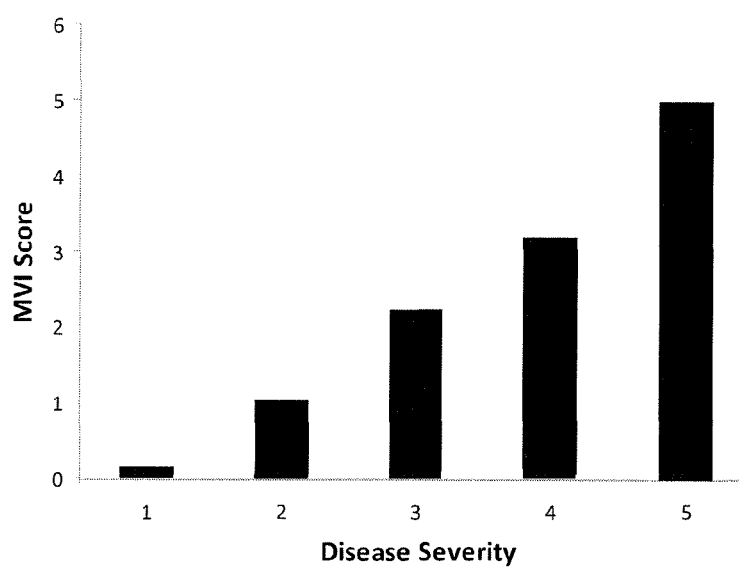

Figure 14. Range of MVI scores for patient groups and controls
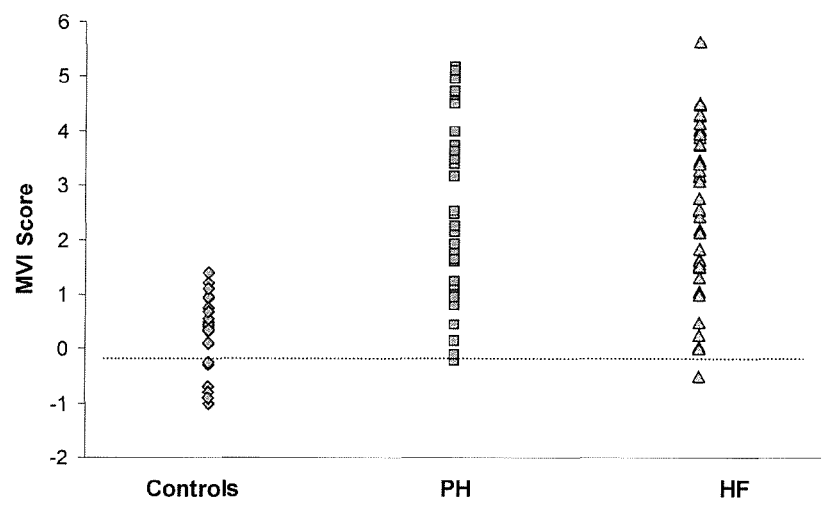

Figure 15a & 15b show tracking disease status over time. a. PAH patient 3 mo. post treatment demonstrating modest improvements in clinical measures and the MVI score. b. HF patients 3 mo. post CRT device implantation demonstrating similar directional changes in MVI score with clinical metrics.
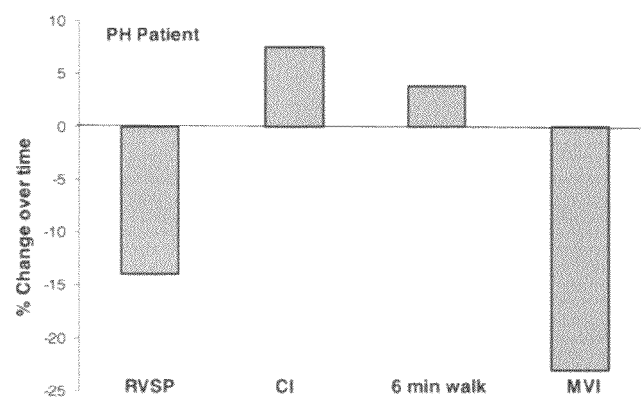
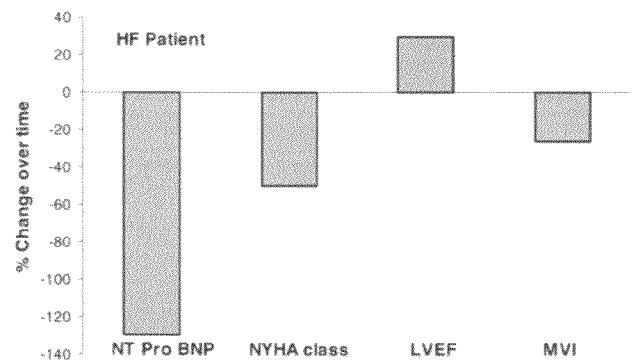

Figure 16. Relationships of MVI score with clinical parameters
16 a,b - HF.
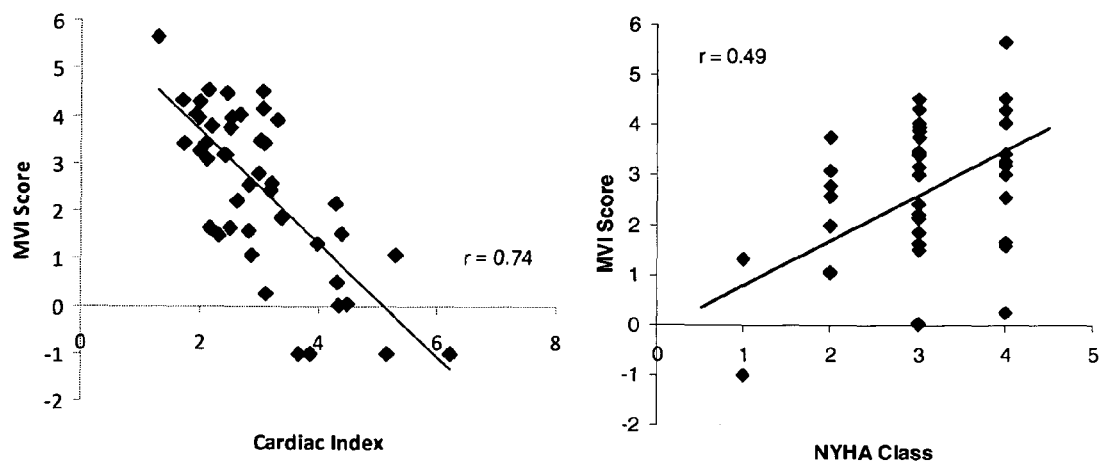
16 c,d - PH.
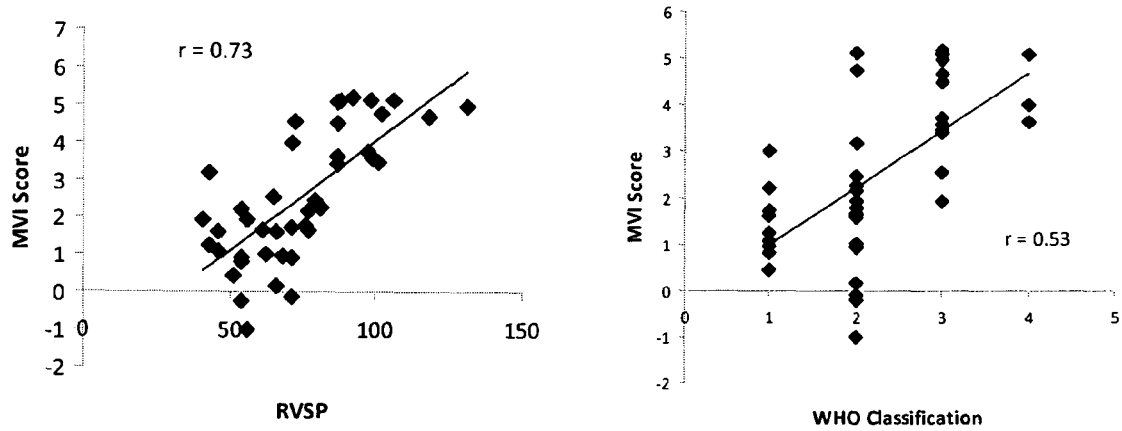

METHOD FOR COMBINING INDIVIDUAL RISK VARIABLES DERIVED FROM CARDIOPULMONARY EXERCISE TESTING INTO A SINGLE VARIABLE

CROSS-REFERENCED TO RELATED APPLICATIONS

This application is a Continuation-In-Part of application Ser. No. 12/209,376, filed Sep. 12, 2008, which is a non-provisional application of Provisional Application No. 60/993,998, filed Sep. 17, 2007, and this application claims priority from those applications which are also deemed incorporated by reference in their entirety in this application.

STATEMENT REGARDING FEDERALLY SPONSORED RESEARCH OR DEVELOPMENT

Not applicable

BACKGROUND OF THE INVENTION

I. Field of the Invention

The present invention relates generally to the field of medical diagnosis and specifically to a process of classifying a patient's functional status to assess the severity of the patient's disease. The disclosed method provides a more sensitive method that is easier to use than currently available classification systems. In addition, the present invention provides feedback during long-term follow-up in patients with chronic diseases.

II. Related Art

Current classification systems include those formulated by the New York Heart Association (NYHA) and by Dr. Karl Weber. The NYHA system places patients in one of four categories based on how much they are limited during physical activity:

| Class | Patient Symptoms |
|---|---|
| Class I (Mild) | No limitation of physical activity. Ordinary physical activity does not cause undue fatigue, palpitation, or dyspnea (shortness of breath). |
| Class II (Mild) | Slight limitation of physical activity. Comfortable at rest, but ordinary physical activity results in fatigue, palpitation, or dyspnea. |
| Class III (Moderate) | Marked limitation of physical activity. Comfortable at rest, but less than ordinary activity causes fatigue, palpitation, or dyspnea. |
| Class IV (Severe) | (Unable to carry out any physical activity without discomfort. Symptoms of cardiac insufficiency at rest. If any physical activity is undertaken, discomfort is increased. |

The Weber classification system is a well established method for categorizing patients into four classes according to peak oxygen consumption or anaerobic threshold.

A major shortcoming of the NYHA system is that it relies on subjective observations by the patient and interpretation of those observations by the physician. Recent scientific literature has identified several flaws in the Weber system, including, for example:

(1) Peak $VO_2$ may be lower than maximally possible (does not represent a true max). A. Gitt, Circulation 2002; 106: p 3079-3084

(2) Sub maximal parameters are more practical than peak $VO_2$, and a more appropriate predictive index. M. Hollenberg, Journal of American College of Cardiology; 2000; 36: p 197-201

Traditionally, maximal cardiopulmonary exercise testing is performed in patients with heart failure as well as other chronic diseases to estimate functional capacity, test for ischemia and to follow general health status. Cardiopulmonary exercise testing is also used in this population clinically to follow response to treatment such as adding new medications, titrating medications, or device therapy. This form of testing is expensive and requires a medical team including MD supervision, RN or exercise specialists, along with a technician to perform the exercise studies. In addition, the equipment necessary includes a number of independent devices including an EKG system which is often integrated into a treadmill or stationary bike, metabolic cart, and a separate oximetry system. Maximal exercise testing is also a test that patients don't look forward to performing, and with heavy exercise there are increased risks.

There is a wealth of literature demonstrating the prognostic value of cardiopulmonary exercise testing, primarily in patients diagnosed with heart failure. (1) Several variables have demonstrated prognostic value including aerobic capacity (2), ventilatory efficiency (3, 4), end tidal carbon dioxide (5) and heart rate recovery (6). While the value of information garnered from this assessment technique is clear, clinical interpretation is presently cumbersome, limiting utilization of the cardiopulmonary exercise test. A formula that included all relevant exercise test variables, appropriately weighted according to prognostic value, and generating a single score would certainly improve clinical interpretation.

The importance of using a multiparametric approach to improving risk stratification has been reported in the literature (7). This article, however, only provides, the receiver operating characteristic curves of three sequential multivariate proportional hazard models. No means are provided to utilize this information in a clinical setting—only the ROC curves are provided, leaving it to the physician to interpret the meaning of multiple CPX, neurohormonal, and echo measurements.

Previously, cardiopulmonary measurements have been made using discrete stages (e.g. Bruce protocol) or ramped protocols that continue until patient symptoms (exhaustion) occur, at which point the test is terminated. The present invention contemplates a simple three-step test (rest, exercise, recovery) which makes use of resting values, average values of exercise measurements, and their difference for multiparametric consideration.

An earlier method used the scientific literature (single source) derived mean value, standard deviation, and a normalizing value (NV), ("the number of Standard Deviations used to define the normal distribution) to calculate a variable called Autononic Balance Index. The NV was used to calculate an ABI coin and the NV was usually set to 2, since this is the classically defined definition of the "normal" range of values for a population measurements".

SUMMARY OF THE INVENTION

In contrast, the present method utilizes two values obtainable independently from the literature—normal value and cutoff point. These and the measured slope (or difference value) are inserted into the equation:

$$1+((\text{measured value}-\text{normal value})/\text{cutoff point}-\text{normal value}).$$

The above equation results in a negative value when the measured value is incrementally beyond the cutoff point, and the computation yields a number that is similar in magnitude for large or small values of normal and cutoff for individual parameters.

The present method insures that truly submaximal protocols can be used to produce valid clinical results. and avoids the need for peak testing to achieve the desired result. The present invention further teaches a method for determining cutoff points retrospectively from disease specific data sets, thereby insuring clinical validity of the multiparametric calculation.

Thus, the present invention, to a large extent, obviates the problems discussed in the foregoing for each of the systems and utilizes the submaximal parameters that improve the predictive power over that of peak $VO_2$ alone. In the present invention, a continuous, numeric multiparametric ranking score or index (MPI) is used to provide an easier to visualize and interpret functional classification for heart disease patients. As indicated, this multiparametric score does not require exercising the patient to a maximal value, but, instead, utilizes gas exchange variables commonly measured during submaximal exercise. While maximal testing will still be required for patients with expected ischemia, a formulaic combination of submaximally obtained variables and peak $VO_2$ will improve clinical interpretation for this population as well.

The literature increasingly has begun to support the idea that a number of gas exchange variables commonly measured during submaximal exercise may be as good or better predictors of general health status and prognosis than values obtained during peak or maximal levels of activity. For example, it is known that ventilation relative to carbon dioxide production ($V_E/VCO_2$) within the first few minutes of exercise is highly predictive of death and is as much or more predictive than peak oxygen consumption. The link between cardiac function and respiratory gas exchange is likely related to high filling pressures which are transferred back to the pulmonary circulation stimulating breathing and altering gas exchange. Thus, other non invasive variables will also change, including the oxygen uptake efficiency slope ($VO_2$/log VE), Chronotropic Response Index (CRI), heart rate recovery, $O_2$ Pulse ($VO_2$/HR), end tidal $CO_2$ values ($PetCO_2$), and breathing pattern (e.g., breathing frequency, fb, and tidal volume, $V_T$, as well as an index of lung compliance, the slope of fb vs carbon dioxide production, $VCO_2$). Thus, it has been found that with worsening disease states, gas exchange will change in parallel, and these changes can form the basis for long term monitoring of the patient's functional status. Based on the above, an individualized set of parameters is selected to be followed.

Outcome Measurement:

After the individualized set of parameters optimally is selected as described, the next step is to make an overall assessment of the patient's functional status over time. In order to appropriately assess the patient's functional status that is, in turn, related closely to adverse patient outcomes, the patient must be stressed, but only normally by mild to moderate exercise, in order to evaluate changes in the sympathetic and parasympathetic components of autonomic balance during dynamic, isotonic exercise and recovery. In other words, a volume load must be placed on the heart in order to assess the cardiopulmonary system's true response to patient activity. It should be noteworthy that it is the same approach with the assessment of cardiac ischemia using the classical ECG stress test. That is, some type of exercise modality must be used in order to stress the heart and create an imbalance in myocardial oxygen supply and demand. Unlike the classical ECG stress test, however, maximal exercise intensity is unnecessary to obtain the measured data. Instead, exercise intensities that reflect those normally experienced by the patient's activities of daily living are used to provide the volume load.

ADVANTAGES

In one study (8), symptom limited CPX tests were performed in 127 patients (age 62.2±14). Anaerobic threshold (AT), determined by the Wasserman "V" slope method, was used for Weber classification. Ventilatory efficiency was derived using sub-maximal exercise data sets by the sub-max linear regression slope of $VE/VCO_2$. Oxygen uptake efficiency was derived using sub-maximal exercise data sets by the sub-max linear regression slope of $V_2$/log VE. The Chronotropic Response Index CRI was derived using sub-maximal exercise data sets by the sub-max linear regression slope of % heart rate reserve/% metabolic reserve (Wilkoff formula). MPI was derived using the above 3 CPX parameters. Percent change amongst Weber Classes was analyzed using MPI and $VO_2$ AT, further quantifying the degree of differentiation between Weber classification, and the results are shown in the following table.

| Select CPX Parameters | Weber A (n = 43) | Weber B/% Δ (n = 47) | Weber C/% Δ (n = 45) | Weber D/% Δ (n = 22) |
| --- | --- | --- | --- | --- |
| $VO_2$ at AT | 17.7 ± 4.8 | 12.4 ± 1.0 (30%) | 9.5 ± .9 (23.4%) | 7.4 ± .5 (22%) |
| MPI | +2.4 ± 2.3 | −.2 ± 2.0 (108% ↓) | −2.3 ± 2.0 (1050% ↓) | −3.7 ± 1.4 (61% ↓) |
| "p" value | | p < .0001 | p < .0001 | p = .006 |

Although the MPI change from Weber A to B marked a + to − change in MPI value, the largest significant transition was observed between Weber classes B and C with further deterioration (>negative value) from Weber functional class C to D. The average % change or inter class discrimination between Weber classes using the cumulative MPI was 406%, as compared to 25% for $VO_2$ AT alone. It will be appreciated that the novel MPI score of the present invention offers a simplified, more sensitive, easier to interpret quantitative means for functional classification. In addition, this is accomplished in a manner that is less stressful to the patient.

In an alternative embodiment, a multiparametric or multivariable system is used that integrates key gas exchange variables or parameters obtained during submaximal exercise into a severity score that is a positive number that ranges from normal (<1) to very severe (>4).

BRIEF DESCRIPTION OF THE DRAWINGS

In the drawings:

FIG. 3 illustrates the organization of the measured data once it is acquired from the cardiopulmonary exercise gas exchange analyzer;

FIG. 4 illustrates the table of data used in part to calculate the Ranking Parameter (RP) used in the present invention;

FIG. 7 illustrates the equations used to calculate the Ranking Parameters (RP);

FIGS. 10A and 10B are plots of multivariable index scores plotted for each subject for pulmonary hypertension (PH) and heart failure (HF) population, respectively, showing the score to be a continuous variable;

FIG. 11A is a plot of the WHO classification for the PH group;

FIG. 11B is a plot of the NYHA classification for the HF group;

FIG. 12 shows data and final model with examples of HF patients according to gas exchange severity;

FIG. 13 shows data and final model with examples of PH patients according to gas exchange severity;

FIG. 14 depicts a range of MVI scores for patient groups and controls;

FIGS. 15A and 15B show tracking disease status over time, (a) PAH patient 3 mo. post treatment demonstrating modest improvements in clinical measures and the MVI score, (b) HF patients 3 mo. post CRT device implantation demonstrating similar directional changes in MVI score with clinical metrics; and FIGS. 16A-16D depict relationships of MVI score with clinical parameters.

DETAILED DESCRIPTION

The following detailed description with respect to patient data is intended to be exemplary of preferred methods of utilizing the concepts of the present invention and are not intended to be exhaustive or limiting in any manner with respect to similar methods and additional or other steps which might occur to those skilled in the art. The following description further utilizes illustrative examples, which are believed sufficient to convey an adequate understanding of the broader concepts to those skilled in the art, and exhaustive examples are believed unnecessary.

General Considerations

The present invention involves a pattern recognition system which includes data gathering, feature extraction and classification aspects. Data is taken by a cardiopulmonary exercise gas exchange analyzer that gathers observations to be classified or described. A feature extraction mechanism computes numeric information from the observations and a classification or description scheme accomplishes the actual job of classifying or describing observations based on the extracted features. These aspects will be described in greater detail.

Data Gathering

The general class of data utilized in the system of the present invention, cardiopulmonary exercise gas exchange measurements, is obtained 1) at rest, 2) during physical exercise testing performed in accordance with a standardized workload protocol as the forcing function to elicit physiologic changes resulting from the workload, and 3) during a short recovery period following exercise termination. Data measured during exercise quantifies how an individual is able to function in the physical world in terms of the physiologic changes that the individual experiences when engaged in the performance of daily physical work.

Physiologic changes are measured using a cardiopulmonary exercise testing system (CPX) to measure selected variables associated with oxygen consumption, $VO_2$, carbon dioxide production, $VCO_2$, end-tidal $CO_2$, $PetCO_2$, ventilation, VE, and heart rate, HR.

The data gathering aspect of the invention involves known techniques and analyses, and the calculations for formulating predictive assessments available, in some cases, in the scientific literature (see the bibliography in References). Importantly, it is aspects of the retrospective analysis of disease specific data sets, the feature extraction mechanism, and the classification scheme from which the invention enables an observer to gain new and valuable insight into the present condition and condition trends in patients. Thus, in accordance with a preferred method, a cardiopulmonary exercise gas exchange analysis is made for each test data set. The performance of such a test is well understood by individuals skilled in the art, and no further explanation of this is believed necessary.

Equipment

Figure 1:
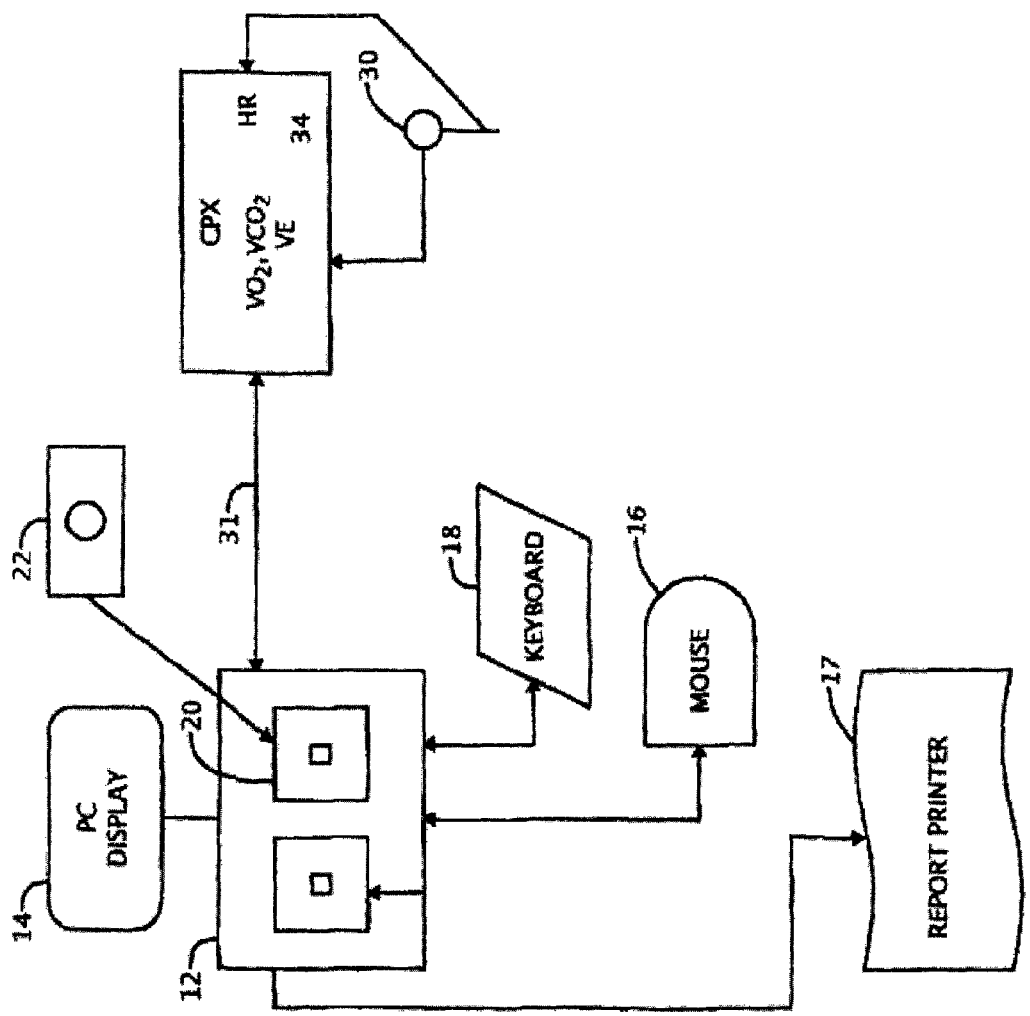
FIG. 1 is a schematic drawing that illustrates the functional components of a CPX testing system usable with the present invention.

With this in mind typical hardware is shown in FIG. 1, which illustrates typical equipment whereby a cardiopulmonary exercise test (CPX) may be conducted and the results displayed in accordance with the method of the present invention. The system is seen to include a data processing device, here shown as a personal computer or PC 12, which includes a video display terminal 14 with associated mouse 16, report printer 17 and a keyboard 18. The system further has a compact disc handler 20 with associated compact disc 22. As is well known in the art, the compact disc handler 20 input/output interfaces comprise read/write devices for reading prerecorded information stored, deleting, adding or changing recorded information, on a machine-readable medium, i.e., a floppy disc, and for providing signals which can be considered as data or operands to be manipulated in accordance with a software program loaded into the RAM or ROM memory (not shown) included in the computing module 12.

The equipment used in the exercise protocol can be a simple stair step of a known height. A CPX testing system 34 interfaces with the subject 30 during operation of the exercise test. The physiological variables may be selected from heart rate (HR), ventilation (VE), rate of oxygen uptake or consumption ($VO_2$) and carbon dioxide production ($VCO_2$) or other variables derived from these basic measurements. Physiological data collected is fed into the computing module 12 via a conductor 31, or other communication device.

Figure 2:
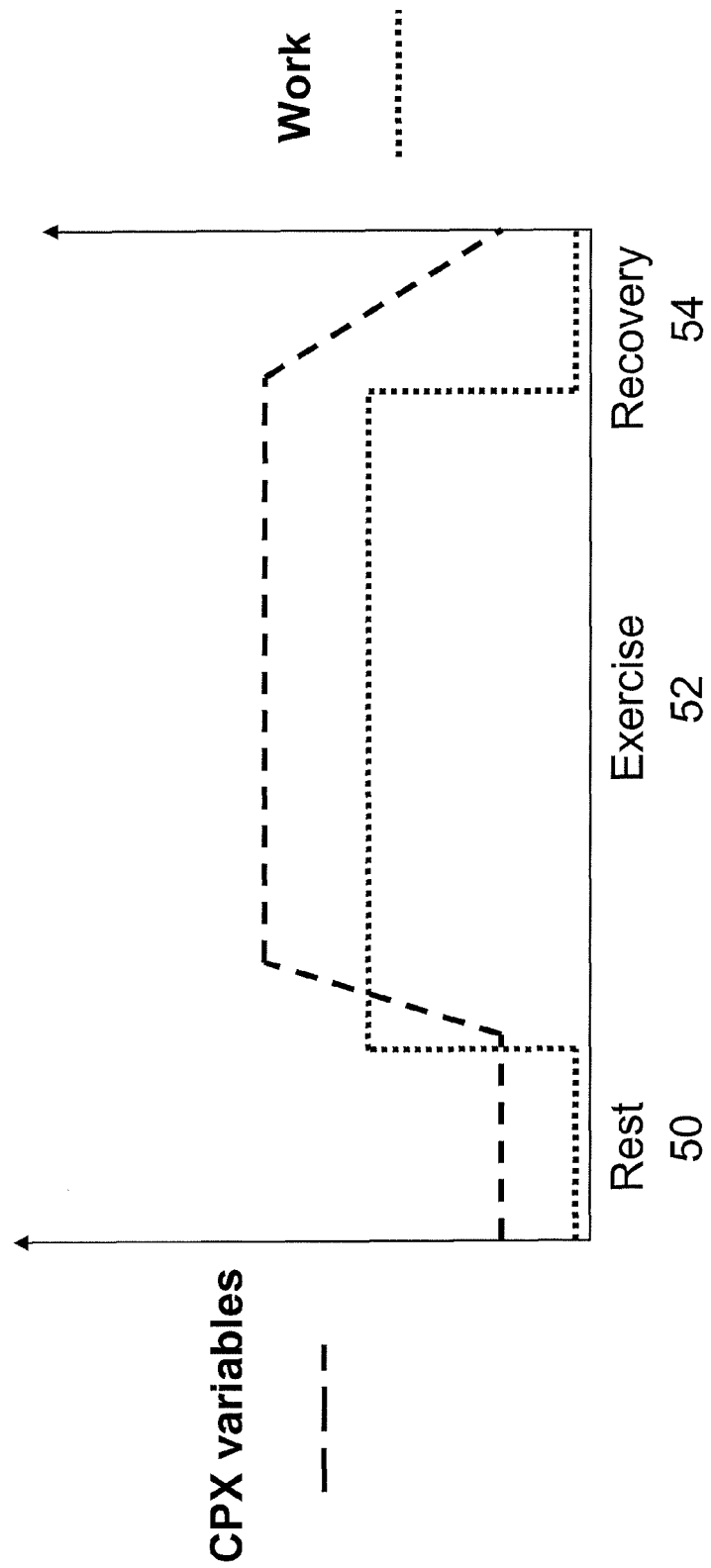
FIG. 2 is a schematic drawing that illustrates one form of exercise protocol that is used to place a volume load on the cardiopulmonary system.

The workload protocol is illustrated in FIG. 2 and is organized into a rest phase 50, an exercise phase 52, and a recovery phase 54. Optionally, the workload may also be quantified by requiring the patient to maintain a desired stepping cadence by the addition of an audible metronome that guides the frequency of the steps taken during the exercise phase.

All data acquired by the CPX system may be stored in a relational database as illustrated in FIG. 3. Most importantly, data for each patient and each test (301) is stored into separate subsets of data (302) representing the rest phase 386, the exercise phase 387, and the recovery phase 388 for use by the feature extraction mechanism.

Feature Extraction

Two types of feature extraction are employed by the system of the present invention: 1) the slope of the line of regression obtained from select data pairs, 2) the difference between the average value of select variables or ratios of variables at rest and during exercise. Representative examples of each are:

1. Slopes—ventilation (VE) vs. carbon dioxide production ($VCO_2$), or ventilatory efficiency slope; oxygen uptake ($VO_2$) vs. log ventilation (VE), or oxygen uptake efficiency slope; % heart rate reserve vs. % metabolic reserve, or CRI; heart rate during one minute of recovery, or heart rate recovery.
2. Difference of average values at rest and during exercise—Partial pressure of end tidal $CO_2$ ($PetCO_2$), Oxygen Pulse ($VO_2/HR$), dead space (VD) to tidal volume (VT), inspiratory drive (VT/Ti)

Feature Extraction—Step 1

Support for the use of statistical pattern recognition also comes from new methods of analyzing cardiopulmonary data published in the scientific literature. From publications listed in the bibliography in the Reference section below, statistical values for the normal value and cutoff point can be obtained for each of the features extracted in Step 1 above. At the present time, these values only exist for the listed slope values, but future uses of such values for slope and for the difference and ratio classes are contemplated by the present invention. In FIG. 4, the available values for normal and cutoff point are stored in table form. It is anticipated that slight changes may be made to the values in FIG. 4 over time based on further studies.

Feature Extraction—Step 2a—Slopes

The next step is to compute the regression line through the select data pairs obtained from the database in FIG. 4. The general form for the regression equation is $$y=a+bx$$

The constant a is the intercept, b is the slope.
The a and b values are chosen so that the sum of squared deviations from the line is minimized. The best line is called the regression line, and the equation describing it is called the regression equation.

Figure 5:
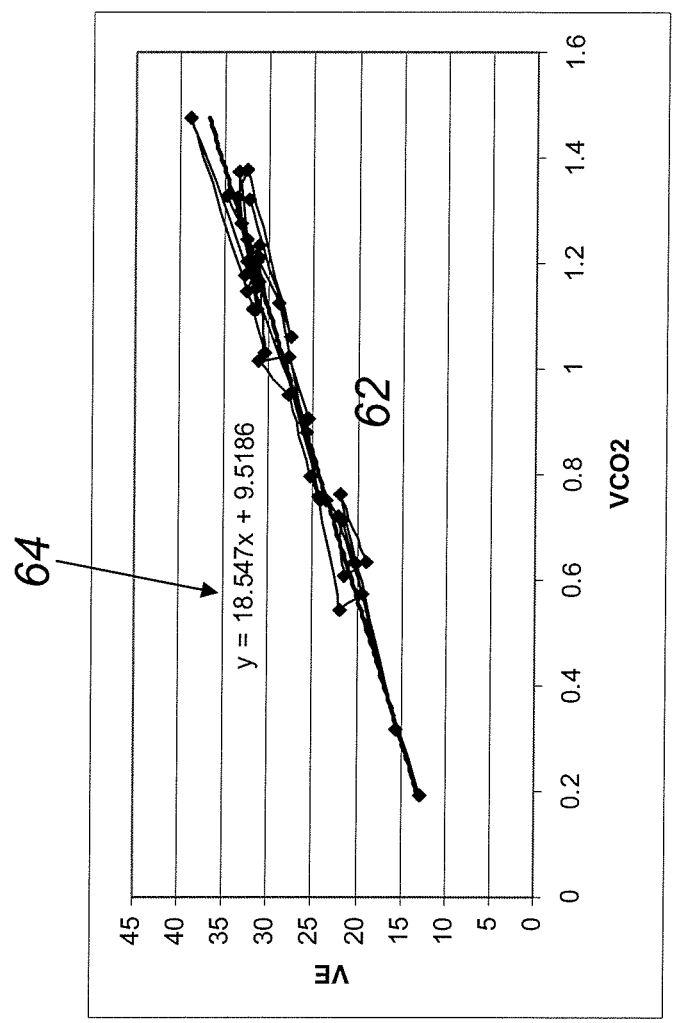
FIG. 5 illustrates the results of a regression analysis of two cardiopulmonary data pairs

In FIG. 5, an example illustrates the measured data for the cardiopulmonary data pairs with the computed line of regression at 62, and the slope and correlation value shown at 64.

Feature Extraction—Step 2B—Deltas

Figure 6:
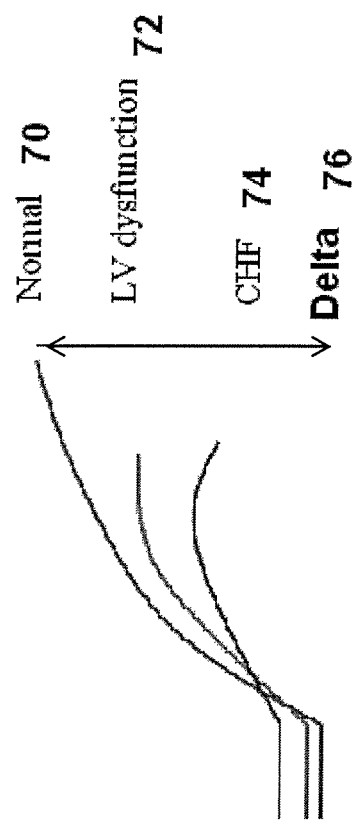
FIG. 6 illustrates the determination of a delta value for normal and diseased patients

In FIG. 6, the idealized response to an increase in workload from the resting phase for $O_2$ pulse ($VO_2/HR$) is illustrated. The normal response is shown at 70, the response for a patient with left ventricle (LV) dysfunction is shown at 72, and the response for a patient with congestive heart failure (CHF) is shown at 74. The delta for the normal response 76 is indicated by the vertical line drawn from the resting value to the normal end of exercise value.

Feature Extraction—Step 3

An individual ranking parameter (RP) is then computed for each of the select data pairs. The RP is calculated using the measured slope value, b, computed in Step 2a and the statistical values obtained from the clinical research or statistical analysis of disease specific data sets for the data pair and stored in the table in FIG. 4. A mitigating factor is that some variables (ventilatory efficiency slope) have high values indicating poor outcome. Some (oxygen uptake efficiency) have low values indicating poor outcome. For the case where "large is bad", the first step is to subtract the measured value from the normal value (NV), or RPve=(NV−measured value)/(Cutoff Point−NV). For the case where "small is bad", RPoeus=(measured value−NV)/(NV−Cutoff Point). By adding 1 to the above, the value of RP is forced to be 0 at a measured value that equals the Cutoff Point (COP). A set of formula equations for calculating various ranking parameters is shown in FIG. 7.

It has been arbitrarily decided that a negative value is undesirable. Thus, a negative RP indicates a poor outcome, a positive RP indicates a positive outcome. The more negative the RP value is, the greater the likelihood of a poor outcome.

Feature Extraction—Step 4

The final step of feature extraction is to calculate the multiparametric index (MPI). The general form of the equation to do this is $$MPI=W_1*RP_1+W_2*RP_2+\ldots+W_n*RP_n$$

Where $W_n$=the weighting factor for the particular ranking parameter $RP_n$.

Both $RP_n$ and $W_n$ are determined by analyzing one or more large disease-specific datasets that include prognostic analysis for adverse-events. Univariate and multivariate Cox regression analysis will be performed to determine which cardiopulmonary exercise testing variables possess prognostic value. For this initial analysis, variables will be assessed as continuous variables. For the multivariate analysis, the forward stepwise method will be employed with entry and removal values set at 0.05 and 0.10, respectively. Receiver operating characteristic curve analysis will then be performed on variables retained in the multivariate regression to determine optimal dichotomous threshold values. Univariate Cox regression will then be employed again to determine the hazard ratios for dichotomous expressions of cardiopulmonary exercise testing variables retained in the multivariate regression. The defined hazard ratios can, optionally, be used as the weighting factors in the MPI. All statistical tests with a p-value <0.05 will be considered significant.

From this analysis, multiple versions of MPIs can be generated. For example, one will include both submaximal and maximal cardiopulmonary exercise test variables to be employed during symptom limited exercise testing. The other MPI would only include variables obtained during submaximal exercise to be used during testing procedures that do not bring a patient to maximal exertion.

Description Scheme—MPI Scale Plot

Figure 8:
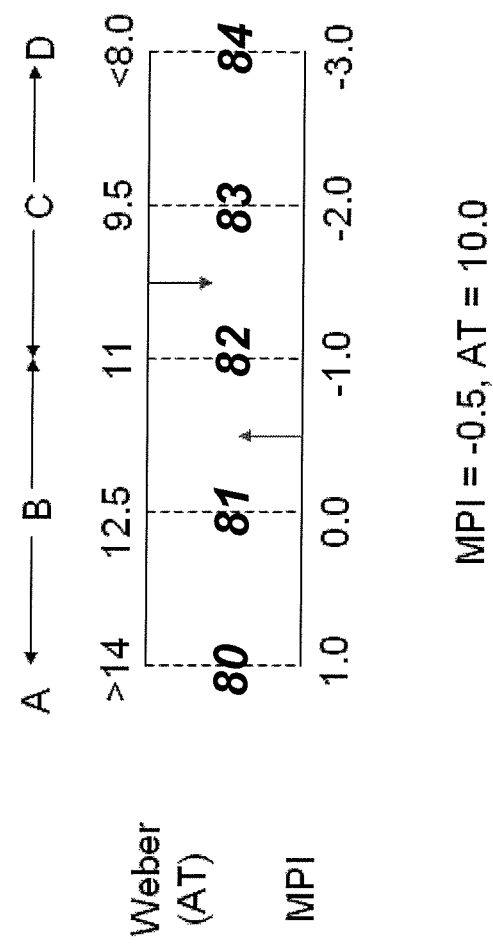
FIG. 8 illustrates a description scheme employed by the present invention for displaying the resultant MPI value from a test with the Weber Class juxtaposed onto the scale.

In order to provide a familiar frame of reference for physicians who use the classification system of the present invention, a preferred method for the description scheme is illustrated in FIG. 8. In the illustrated case, the Weber system utilizing anaerobic threshold is combined with a numerical scale for displaying the MPI value for the current patient test. The delineation between Weber classes and MPI values are shown at 80,81,82,83 and 84. Also illustrated is one example of how to display the calculated values of MPI and AT and their scale locations.

Description Scheme—Trend Plot

Figure 9:
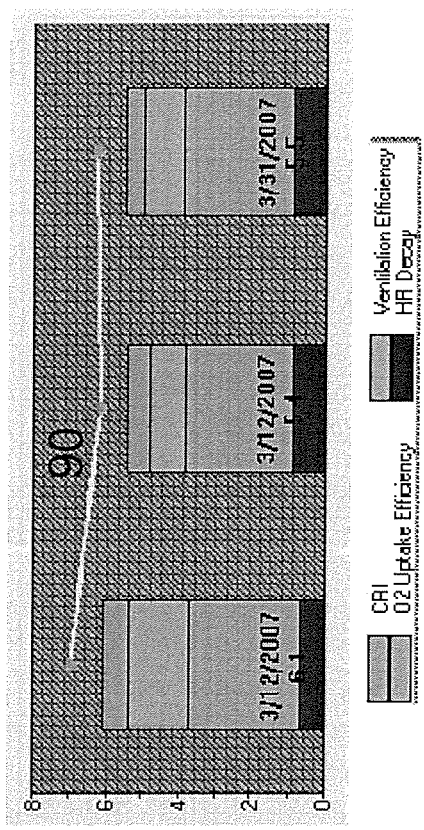
FIG. 9 illustrates a trend plot of time-sequential MPI test values

Of course, an important aspect of the value of the system of the present invention is the ability to provide a rapid assessment of the effect of any given therapy over time as by, for example, using a trend plot. One example of a trend plot for MPI value over time is illustrated in the bar chart in FIG. 9. In this example, the individual values of the RP are scaled and stacked to form a bar, and, in this manner, the MPI value determines the vertical height of each bar. The MPI value and date is then displayed in relationship to the bar. In this example, a line at 90 displays the numeric trend. However, it will be understood that there is no limitation intended in terms of the type of graph utilized or visual effects employed.

In an alternative embodiment, a multivariable gas exchange index (MVI) is used that integrates key gas exchange variables obtained during submaximal exercise into a severity score that ranges from normal (<1) to very severe (>=4). As will be described in detail below, to demonstrate the usefulness of this index, the MVI is applied to 2 patient groups pulmonary arterial hypertension (PAH), n=42 and heart failure (HF), n=47) as well as to age matched healthy controls (n=25). It demonstrates that this score tracks WHO classification and right ventricular systolic pressure (RVSP) in PAH (r=0.53 and 0.73) and NYHA and cardiac index (CI) in HF (r=0.49 and 0.74). In addition this index demonstrates a stronger relationship than any single gas exchange variable alone to these clinical indices and has a specific modifier based on the abrupt reversal pattern of end tidal $CO_2$ with exercise ($PetCO_2$), representative of exercise induced PH. The MVI provides an easily adjustable multivariable index based on light, submaximal exercise gas exchange to simplify data interpretation in the PAH and HF populations.

As indicated above and well accepted in the field, the lungs are linked hemodynamically in series with the heart, share a common surface area, are exposed to similar intrathoracic pressure changes during breathing, compete for intrathoracic space and receive nearly 100% of the cardiac output. Receptors in the heart influence breathing patterns, while neural pathways in the lungs in-turn may influence cardiac function (e.g., heart rate). Small increases in metabolic demand (e.g., exercise) enhance these cardiopulmonary interactions. Thus, diseases that primarily influence the lungs or the heart significantly impact the other organ system (Olson 2006, Lalande 2009). This can be especially observed in patients with pulmonary arterial hypertension (PAH) where right heart failure evolves and in patients with left heart failure (HF) where significant changes occur in lung mechanics, ventilatory control and ultimately in respiratory gas exchange. In both these patient groups gas exchange abnormalities are often present at rest, but are accentuated with the challenges of exercise. Thus, non-invasive measures of cardiopulmonary gas exchange obtained during exercise have become a relatively common means to assess disease severity, prognosis as well as response to therapy. However, despite the availability of data to the contrary, non-invasive respiratory gas exchange information has generally heretofore been relatively poorly understood and under utilized in day to day clinical practice.

There have been a number of impediments to more extensive utilization of exercise respiratory gas exchange. This includes issues such as the large number of variables that are produced from typical commercially based systems, the somewhat broad range of normal values (influenced by age, gender, fitness, obesity, anxiety, body size, etc.), co-morbidities that may influence the data, the complexities and expense that have been associated with comprehensive clinically based cardiopulmonary exercise testing and difficulties and anxieties associated with maximal testing of often brittle patient populations.

However, more recently, non-invasive commercially available gas exchange systems have been developed that are simpler, self calibrating, with a lighter, less complicated patient interface. In addition, it is becoming clear, as emphasized in relation to the embodiment above, that gas exchange data other than peak oxygen consumption ($VO_{2max}$ or $VO_{2peak}$) that can be obtained from light or submaximal exercise (e.g., $V_E/VCO_2$, OUES, $PetCO_2$) as a slope or change from rest, may be as good or in some cases more prognostic, reproducible and sensitive than those obtained from maximal exercise testing and provoke less patient anxiety at reduced cost. We have previously demonstrated that blending simpler devices with minimized, sub-maximal protocols is well liked by patients, with the gas exchange data adequately separating both PAH and HF patients from healthy populations and according to disease severity.

To further simplify cardiopulmonary gas exchange for clinical use in the PAH and HF populations, this embodiment introduces a multivariable index (MVI) that takes into account the key gas exchange variables obtained during exercise that have been shown to be associated with these disease entities. The value of a multiparameter index or score is presented in detail above. That approach to creating a novel non-invasive gas exchange severity score from submaximal data for both PAH and HF has been described and tested in patient groups. The present embodiment includes a comprehensive and systematic approach that provides a clear framework for tracking PAH patients; appears to track disease status in the HF population and provides a modifier for exercise induced PH.

The multivariable index (MVI) of the invention produces a single numerical result for scoring gas exchange data. It was developed based on previously reported data from the applicants' laboratory and others. Six variables were identified that have been shown to track disease severity and/or prognosis in PAH and in the HF populations and which can be obtained form rest and light, submaximal exercise. Many of these variables have published cut off values or ranges that are associated with higher risk. This includes 1) the ventilatory equivalents for carbon dioxide production ($V_E/VCO_2$) or breathing efficiency, 2) the oxygen uptake efficiency slope (OUES), 3) oxygen saturation ($SaO_2$), 4) the resting $PetCO_2$, 5) the change in $PetCO_2$ with exercise, 6) a calculated gas exchange variable as an index for pulmonary capacitance ($P_{CAP}$) which is the oxygen pulse multiplied by $PetCO_2$ ($O_{2pulse} \times PetCO_2$) that tracks invasive measures of pulmonary capacitance and a modifying variable based on the slope of change in the inflection of $PetCO_2$ from rest to light exercise, as described in co-pending application Ser. No. 12/567,005, entitled "A Pattern Recognition System for Classifying the Functional Status of Patients With Pulmonary Arterial Hypertension", filed Sep. 25, 2009 and assigned to the same assignee as the present application. That application is deemed incorporated by reference herein in its entirety. That application applies a different calculated multiparametric index ($MPI_{PH}$) for diagnosing the presence of and classifying the functional status of patients with pulmonary hypertension.

This final modifier has been suggested to reflect more severe exercise induced changes in pulmonary vascular pressure and/or potential shunting through a PFO or intrapulmonary shunts due to high pressures. There is some redundancy purposefully built into the MVI for variables most strongly associated with clinical measures, but yet retaining the ultimate goal of a single score that quantifies the severity of derangement in gas exchange rather than a formal surrogate to these other clinical markers. In fact, in accordance with the invention, in many cases gas exchange data from light exercise may give a more important measure of integrated central hemodynamic function than the more commonly used "gold standards" for assessing and quantifying disease severity.

Table 1 describes the variable set used, the normal values (from the literature), and the delta value, or the difference between the normal value and the risk cutoff point. The rows under "measured" are measured values of the variable in that column ranging in severity from normal to severe-very severe. The column immediately to the right of each variable column is the computed value of the individual variable index (IVI). Recognizing that some variables vary directly in severity from low to high (e.g., $V_E/VCO_2$ slope) and some variables vary in severity inversely from high to low (e.g., OUES), the IVI is computed using; e.g., for $V_E/VCO_2$ slope:=$((1+((V_E\text{slope}NV-\text{Measured})/V_E\text{slope}D))*-1)+1$; and for OUES:=$((1+((\text{Measured}-\text{OUES}NV)/\text{OUES}D))*-1)+1$.

TABLE 1

Model showing individual variables (individual variable index, IVI) that make up the multivariable scoring system.
Normal values from literature with delta representing the difference between Normal and the risk cutoff for each IVI.

|  |  | IVI |  | IVI |  | IVI |  | IVI |  | IVI |  | IVI | Cumulative |
|---|---|---|---|---|---|---|---|---|---|---|---|---|---|
| Normal Value | Rest PetCO2 | 40 | Δ PETCO2 | 3.6 | SaO2 | 94 |  | OUES | 1.6 | VE/VCO2 | 26 | PAP capacitance | 400 |
| Delta |  | 5 |  | 1.8 |  | 1.8 |  | 4 |  | 0.24 |  | 7 | 40 |
| Cutoff | >40 |  | >3.6 |  | >94 |  |  | >1.6 |  | <26 |  | >400 |  |
| Normal | 40 | 0.00 | 3.6 | 0.00 | 94 | 0.00 |  | 1.6 | 0.00 | 26 | 0.00 | 400 | 0.00 | 0.00 |
| Normal-Mild | 40-<35 |  | 3.6-<1.8 |  | 94-<90 |  |  | 1.6-<1.36 |  | 26-<33 |  | 400-<360 |  |
|  | 35 | 1.00 | 1.8 | 1.00 | 90 | 1.00 |  | 1.36 | 1.00 | 33 | 1.00 | 360 | 1.00 | 6.00 |
| Mild-Moderate | 35-<30 |  | 1.8-<0 |  | 90-<86 |  |  | 1.36-<1.12 |  | 33-<40 |  | 360-<320 |  |
|  | 30 | 2.00 | 0 | 2.00 | 86 | 2.00 |  | 1.12 | 2.00 | 40 | 2.00 | 320 | 2.00 | 12.00 |
| Moderate Severe | 30-<25 |  | 0-<-1.8 |  | 86-<82 |  |  | 1.12-<.88 |  | 40-<47 |  | 320-<280 |  |
|  | 25 | 3.00 | -1.8 | 3.00 | 82 | 3.00 |  | 0.88 | 3.00 | 47 | 3.00 | 280 | 3.00 | 18.00 |
| Severe-Very Severe | 25-<20 |  | "-1.8-<-3.6" |  | 82-<78 |  |  | .88-<.64 |  | 47-<54 |  | 280-<2400 |  |
|  | 20 | 4.00 | -3.6 | 4.00 | 78 | 4.00 |  | 0.64 | 4.00 | 54 | 4.00 | 240 | 4.00 | 24.00 |

|  |  |  |  |  |  |  |  |  |  |  |  |  | CUM IVI | MVI = Cum IVI/6 |
|---|---|---|---|---|---|---|---|---|---|---|---|---|---|---|
| Normal | 40 | 0.00 | 3.6 | 0.00 | 94 | 0.00 | 1.6 | 0.00 | 26 | 0.00 | 360 | 0.00 | 0.00 | 0.00 |
| Normal-Mild | 35 | 1.00 | 1.8 | 1.00 | 90 | 1.00 | 1.36 | 1.00 | 33 | 1.00 | 320 | 1.00 | 6.00 | 1.00 |
| Mild-Moderate | 30 | 2.00 | 0 | 2.00 | 86 | 2.00 | 1.12 | 2.00 | 40 | 2.00 | 280 | 2.00 | 12.00 | 2.00 |
| Moderate-Severe | 25 | 3.00 | -1.8 | 3.00 | 82 | 3.00 | 0.88 | 3.00 | 47 | 3.00 | 240 | 3.00 | 18.00 | 3.00 |
| Severe-Very Severe | 20 | 4.00 | -3.6 | 4.00 | 78 | 4.00 | 0.64 | 4.00 | 54 | 4.00 | 200 | 4.00 | 24.00 | 4.00 |

In this manner, if the measured=NV (normal value), the value of the IVI=0. If the measured equals the risk cutoff point, the value of IVI=1. IVI's that result in MVI's greater than 4.0 are scored as Severe-Very Severe. Normal subjects have MVI values less than 1.0 and can be negative as well. It can be seen that the 6 variable MVI values closely resemble the NYHA classification system as shown in table 2.

TABLE 2

Baseline multivariable index (MVI) scoring system

| MVI = CUM IVI/6 | Range | Severity | NYHA |
|---|---|---|---|
| 0.00 | <1 | Normal | n/a |
| 1.00 | 1 to <2 | Normal-Mild | I |
| 2.00 | 2 to <3 | Mild-Moderate | II |
| 3.00 | 3 to <4 | Moderate-Severe | III |
| 4.00 | >=4 | Severe-Very Severe | IV |

Another feature of the MVI classification system is the ability to impart a greater weight to IVI's. It is proposed that this feature would allow for the evolution of disease specific MVI's. For example, the individual IVI for $P_{CAP}$ has been "double counted", or multiplied by a factor of 2 in the Cumulative IVI since it tends to track disease severity more closely than the other measures. The MVI was then obtained by dividing the Cumulative IVI by 7, rather than 6 for the un-weighted MVI. The effect of doing so can be observed in table 3. Since it is not possible to impart meaning to negative MVI values (other than that the patient is normal), for comparative purposes, any MVI value less than −1 was arbitrarily set to −1.

TABLE 3

MVI scoring system weighted for $P_{CAP}$

| CUM IVI | MVI = CUM IVI/7 | Range | Severity | NYHA |
|---|---|---|---|---|
| 0.00 | 0.00 | <1 | Normal | n/a |
| 7.00 | 1.00 | 1 to <2 | Normal-Mild | I |
| 14.00 | 2.00 | 2 to <3 | Mild-Moderate | II |
| 21.00 | 3.00 | 3 to <4 | Moderate-Severe | III |
| 28.00 | 4.00 | >=4 | Severe-Very Severe | IV |

The MVI classification system also has the ability to apply additional modifiers. It has been demonstrated in the literature (and our co-pending application Ser. No. 12/567,005) that an abrupt fall in $PetCO_2$ (steep slope) with exercise is itself a gauge of severity of PH. The accuracy of classification is increased by increasing the MVI score by values proportional to the magnitude and slope of change in $PetCO_2$ during exercise (see Table 4 below). Adding the modifier for the $PetCO_2$ patterns increased the severity score for individual subjects without altering the MVI scale range. In addition, adding the $MVI_{PH}$ modifier to the MVI score consistently improved the correlations between the index and other clinical variables in both PAH and in the HF populations.

TABLE 4

MVI scoring system weighted for the slope of change and magnitude of change in $PetCO_2$ (indicative of exercise induced PH)

| $MVI_{PH}$ | Modifier = |
|---|---|
| >=0 | 0.00 |
| <0 and >-5 | 0.50 |
| >=-5 and >-10 | 0.75 |
| <=-10 | 1.00 |

Results of Testing the Model in Patient Groups.

The use of the final MVI score was examined in three populations from previously published studies (see table 5 below). This included patients with primarily PAH and classic systolic HF along with healthy subjects of similar age ranges. The PAH patients were recruited with known pulmonary hypertension through our PH Clinic and performed a light submaximal 3 min step test after collecting 2 min of resting data, while the HF patients performed submaximal cycling ergometry (similar levels of perceived exertion). Control subjects performed a combination of the light step testing and submaximal cycle ergometry. Both patient groups had a range of disease severity levels and were typically on standard therapy. Breath by breath gas exchange data were collected for all populations using the Shape Medical Systems, Inc. simplified gas exchange system and slopes (e.g., $V_E/VCO_2$) were determined by linear regression. For the HF group, the thirty second averages of the last stage of exercise and the 30 second averages of the end of the rest period were used for a two point slope equation. Thirty second averages at the end of exercise were used to calculate the other IVI variables.

TABLE 5

Subject Characteristics

|  | Controls | PAH | Heart Failure |
|---|---|---|---|
| N Number (% female) | 25 (80%) | 40 (80%) | 45/(13%) |
| Age (years) | 51 ± 15 | 50 ± 13 | 54 ± 8 |
| Height (cm) | 167.8 ± 8.2 | 167.7 ± 7.0 | 174.9 ± 8 |
| Weight (kg) | 70.1 ± 12.7 | 75.8 ± 16.5 | 86.6 ± 16.3 |
| HF etiology Ischemic/dilated (n) |  |  | 23/22 |
| NYHA Class (I/II/III/IV) |  |  | 5/7/23/10 |
| LVEF (%) | 61 ± 7 | 64 ± 7.3 | 20 ± 6 |
| NT Pro BNP/BNP |  | 770 ± 1239 | 852 ± 2341 |
| Cardiac Index | 3.0 ± 0.3 | 3.1 ± 0.7 | 1.9 ± 0.6 |

The ranges for MVI for each database are illustrated in FIG. 10A (PAH) and 1b (HF). When compared to the WHO or NYHA classification for the respective patient cohorts, (FIGS. 11A and 11B), it can be seen that the clinical classification results in "data aliasing" vs the MVI score which gives a continuous variable. FIGS. 12 and 13 give examples of individual PAH and HF patients over the range of scores obtained by the final MVI model. This also includes a healthy normal individual. FIG. 14 shows the ranges of MVI scores for the Control, PH, and HF populations. It should be noted that the patient populations presented have benefited from medical therapy and thus overlap exists across populations.

FIG. 15 shows an example of a PH patient and a HF patient before and after intervention (medication titration in the PH patient and cardiac resynchronization therapy in the HF patient). Both patients demonstrated benefits in clinical measures (RVSP, CI and 6 min walk in PH patient and NT Pro BNP, NYHA class and LVEF in the HF patient), with improvements in the MVI score. The overall relationship between the MVI score to RVSP and WHO classification in PAH (FIGS. 16A and 16B) and CI and NYHA class in HF were also examined. The score was more highly correlated with the physiological measures vs the more subjective functional classifications. Individual correlations for the components of the MVI score with CI and RVSP are provided in Table 6. PetCO$_2$, OUES, $V_E/VCO_2$ slope, $P_{CAP}$ all demonstrated significant relationships with CI in HF and RVSP in PAH patients with less significant relationships between these gas exchange measures and NYHA or WHO classification. Modest improvements over the majority of variables was observed using the MVI score.

| PAH etiology | | | |
|---|---|---|---|
| Idiopathic | — | 25 (63%) | |
| Hereditary | — | 4 (10%) | |
| Associated with diet drug use | — | 2 (5%) | |
| Portopulmonary Hypertension | — | 1 (2%) | |
| Associated with connective tissue disease | — | 8 (20%) | |
| Functional Class (WHO) (I/II/III/IV) | — | 7/20/11/2 | |
| RV Pressure (mmHg) | 26 ± 4 | 76 ± 23 | 49 ± 18 |

This embodiment provides a comprehensive multivariable index (MVI) scoring system to quantify gas exchange severity from light submaximal exercise data specific to populations with pulmonary vascular disease and demonstrate its utility in patients with PAH and systolic heart failure. The MVI allows a simple approach to integrating important gas exchange variables into a single conceptual score designed to track disease severity. The score is further weighted towards variables that reflect more severe hemodynamic derangement during exercise and is based on exercise loads that are commonly experienced by patients in daily activities. This score while designed to reflect gas exchange abnormalities and not necessarily other clinical tracking variables, shows a modest association with clinically used classification schemes as well as catheter or echo based measures.

It has become clear that a number of submaximal responses to exercise are as or more predictive for morbidity and mortality in the HF population and many of these non invasive submaximal measures are slopes or changes from rest and thus relatively insensitive to intensity of exercise, and in many cases being more reproducible. Metrics that have been shown to be highly prognostic and sensitive to disease severity include the ventilatory efficiency, the oxygen uptake efficiency slope, the absolute or change in PetCO$_2$, the change in O$_2$pulse, oxygen saturation—SaO$_2$.

Ventilatory efficiency has been linked to a high dead space ventilation—due mostly to a more rapid shallow breathing pattern, combined with a greater relative hyperventilation. It increases progressively with disease severity in both PAH and HF. PetCO$_2$ appears to track the rise in pulmonary vascular pressures with exercise, especially in PH patients, likely due to both a pressure induced increase in ventilation, but also due to increasing ventilation and perfusion inhomogeneities in the lungs and is typically inversely related with $V_E/VCO_2$ slope suggesting in general they provide similar information. Oxygen pulse (VO$_2$/HR) is essentially the stroke volume multiplied times oxygen extraction, but appears to track stroke volume relatively well. Using invasive or technical echocardiography based measures, various techniques have been used to quantify a value representing pulmonary vascular capacitance (change in stroke volume relative to change in pulmonary pressures), which has been shown to be predictive of mortality in the PAH population. A non-invasive estimate of pulmonary capacitance (Pcap or PVcap) based on the equation (O$_2$pulse—as an estimate of stroke volume)×(PetCO$_2$—as an estimate of pulmonary vascular pressure) was compared to catheter based measures obtained during exercise and a strong relationship was found in the HF population. The gas exchange derived $P_{CAP}$ also demonstrated a relatively strong relationship with our clinical metrics in this study with only modest improvements using the complete MVI score. However, many gas exchange variables tend to change in concert and in particular measures of $PetCO_2$ and/or $V_E/VCO_2$ slope appear to be the variables that are most highly associated with clinical metrics and are counted or weighted heavily in the present MVI scoring system, while at the same time allowing for other variables (e.g., $SaO_2$) to contribute in a positive or negative way to the final score. In addition, such an approach to amalgamating variables tends to reduce noise. Thus the MVI score is weighted heavily towards factors which elevate dead space ventilation, inhibit a rise in stroke volume, cause a more rapid and shallow breathing pattern and to a lesser extent cause oxygen desaturation with exercise (e.g., shunt, low VA/Qc regions, diffusion limitation). In addition, the score is increased if the negative rate of change in $PetCO_2$ with exercise is excessive.

The MVI score of the present invention demonstrates an improvement in the association with clinical measures over any single variable. However, while the score has been purposefully weighted to track disease severity in the PAH and HF populations, the original purpose was to create a gas exchange severity score and thus to some extent to be independent of other clinical measures. Thus, while the MVI score will generally track other clinical or physiological measures associated with disease severity, there may not necessarily be a strong relationship with these clinical measures for a variety of reasons. For example, in some PAH patients, creating artificial shunts may reduce symptoms, but at the same time cause greater gas exchange abnormalities with exercise, making the gas exchange severity score worse. Therefore, the present system takes an intuitive approach rather than a statistical approach to creating the scoring system as the score should be able to serve as an independent way to track disease and because there is no perfect gold standard for which to develop the statistical approach. In addition, other measures such as NYHA or WHO classification remain quite subjective.

Other problems exist with the current "gold standards", including a large variability in both echo and cath-based measures and cath-based measures tend to have a number of limitations and often assumptions, particularly when cardiac hemodynamics are assessed during exercise. The MVI of the present invention is a comprehensive and adaptable gas exchange severity score that is not dependent on maximal exercise values and provides an independent value for grading and tracking disease relative to other clinical measures. With simplified techniques for quantifying gas exchange and the growing awareness that values obtained with light submaximal exercise are as prognostic as maximally obtained values in several populations, cardiopulmonary gas exchange could be easily adapted to many clinical areas as more of a "vital sign" rather than the more comprehensive and elaborate approach to testing that has classically been used, particularly in the HF and PH populations where ischemia detection is not a primary end point. Adding a gas exchange severity score to this simplified approach for screening and tracking patients further simplifies testing and reduces the need for specific expertise in cardio respiratory physiology. Having a scoring system such as the MVI allows a more comprehensive metric than "$VO_{2peak}$" and a scaling system that is more similar to other scoring systems (e.g. NYHA or WHO classification) that are familiar to clinical experts.

The MVI gas exchange severity score provides a simple means to rapidly assess disease risk and response to therapy in HF and PH patients and provides an overall assessment of integrative cardiac hemodynamics. The score reduces the complications of having to understand a large number of variables, eliminates the need for interpretation, accounts for variables with multiple directional changes, avoids noise that can be created by one value being abnormal vs the other values and provides an easily identifiable numbering scheme for physicians to track.

The invention has been described in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as the equipment details and operating procedures can be accomplished without departing from the scope of the invention itself.

PUBLICATION REFERENCE LIST

1. Gibbons R J, Balady G J, Timothy B J, et al. ACC/AHA 2002 guideline update for exercise testing: summary article. A report of the American College of Cardiology/American Heart Association Task Force on Practice Guidelines (Committee to Update the 1997 Exercise Testing Guidelines). J Am Coll Cardiol 2002; 40:1531-40.
2. Arena R, Myers J, Williams M A, et al. Assessment of functional capacity in clinical and research settings: a scientific statement from the American Heart Association Committee on Exercise, Rehabilitation, and Prevention of the Council on Clinical Cardiology and the Council on Cardiovascular Nursing. Circulation 2007; 116:329-43.
3. Arena R, Myers J, Guazzi M. The clinical and research applications of aerobic capacity and ventilatory efficiency in heart failure: an evidence-based review. Heart Fail Rev 2008; 13:245-69.
4. Mancini D M, Eisen H, Kussmaul W, Mull R, Edmunds L H, Jr., Wilson J R. Value of peak exercise oxygen consumption for optimal timing of cardiac transplantation in ambulatory patients with heart failure. Circulation 1991; 83:778-86.
5. Arena R, Myers J, Abella J, et al. Development of a Ventilatory Classification System in Patients With Heart Failure. Circulation 2007; 115:2410-7.
6. Francis D P, Shamim W, Davies L C, et al. Cardiopulmonary exercise testing for prognosis in chronic heart failure: continuous and independent prognostic value from VE/VCO(2) slope and peak VO(2). Eur Heart J 2000; 21:154-61.
7. Scardozi A B, et al. Multiparametric Risk Stratification in Patients With Mild to Chronic Heart Failure. Journal of Cardiac Failure 2007; 13:445-51.

MPI REFERENCES

1. VE Efficiency Slope:
Normal Values:
(a) 25.6±3.2; N=144;
Reference:
Arena R, J Myers, J Abella, M A Peberdy, D Bensimhon, P Chase, M Gauzzi. Development of a ventilation classification system in patients with heart failure. *Circulation*, 2007; 115:2410-2417.
(b) 26.2±4.0; N=101;
Reference:
Kleber F X, G Vietzke, K D Wernecke, U Bauer, C Opitz, R Wensel, A Sperfeld, S Glaser. Impairment of ventilatory efficiency in heart failure: Prognostic impact. *Circulation*, 2000; 101:2803-2809.

(c) 26.5±3.8; N=83;
Reference:
Ponikowski P, D P Francis, M F Piepoli, L Ceri Davies, T P Chua, C H Davos, V Florea, W Banasiak, P A Poole-Wilson, A J S Coats, S D Anker. Enhanced ventilatory response to exercise in patients with chronic heart failure and preserved exercise tolerance: Marker of abnormal cardiorespiratory reflex control and predictor of poor prognosis. *Circulation,* 2001:103:967-972.
Mean normal value+26.1; N=328 subjects
Cut-Off Values for HF Patients:
(a) 35.0; N=600
Reference:
Corra U, A Mezzani, E Bosimini, F Scapellato, A Imparato, P Giannuzzi. Ventilatory response to exercise improves risk stratification in patients with chronic heart failure and intermediate functional capacity. *Am Heart J,* 2002; 143 (3):418-426.
(b) 34.2 with ishemic disease and 34.5 with non-ischemic disease; N=268
Reference:
Arena R, J Myers, J Abella, M A Peberdy. Influence of heart failure etiology on the prognostic value of peak oxygen consumption and minute ventilation/carbon dioxide production slope. *Chest,* 2005; 128:2812-2817.
(c) 36.2; N=288
Reference:
Guazzi M, R Arena, A Ascione, M Piepoli, M D Guazzi. Exercise oscillatory breathing and increased ventilation to carbon dioxide production slope in heart failure: An unfavorable combination with high prognostic value. *Am Heart J,* 2007; 153:859-867.
Mean cut-off point=35.0; N=1156 HF patients
Note: The Ventilation Efficiency Classification reference by Arena and Meyers is also needed as a reference in the software. I believe you have this PDF file already (is in the reference list).
2. Oxygen Uptake Efficiency Slope (ODES)
Normal Values:
(a) 2.12±0.33; N=415;
Reference:
A. Thomas McRae III, James B. Young, M L. Alkotob, Claire E. Pothier Snader, Eugene H. Blackstone, Michael S. Lauer. The Oxygen Efficiency Slope as a Predictor of Mortality in Chronic Heart Failure. J Amer. College Cardioolgy; Vol 43 (5) Suppl; 856-3; 2002.
(b) 2.33±0.5 men; 1.60 women; N=998 total
Reference:
M. Holenberg and Ira B. Tager. Oxygen Uptake Efficiency Slope: An Index of Exercise Performance and Cardiopulmonary Reserve Requiring Only Submaximal Exercise. J. Am Coll Cardiology; 2000; 36:194-201.
Cut-Off Values for HF Patients:
(a) 1.4; N=341
Reference:
Arena R, J Myers, L Hsu, M A Peberdy, S Pinkstaff, D Bensimhon, P Chase, M Vicenzi, M Guazzi. The minute ventilation/carbon dioxide production slope is prognostically superior to the oxygen uptake efficiency slope. *J Cardiac Fail,* 2007; 13(6):462-469.
(b) 1.47; N=243
Reference:
Davies L C, R Wensel, P Georgiadou, M Cicoira, A J S Coats, M F Piepoli, D P Francis. Enhanced prognostic value from cardiopulmonary exercise testing in chronic heart failure by non-linear analysis: oxygen uptake efficiency slope. *E Heart J,* 2006; 27:684-690.
(c) 1.31; N=1245
Reference:
A. Thomas McRae III, James B. Young, M L. Alkotob, Claire E. Pothier Snader, Eugene H. Blackstone, Michael S. Lauer. The Oxygen Efficiency Slope as a Predictor of Mortality in Chronic Heart Failure. J Amer. College Cardioolgy; Vol 43 (5) Suppl; 856-3; 2002.
Mean "Cut-off" point=1.39
3. Heart Rate Recovery
Normal Values:
(a) 33±9; N=4633
Reference:
Watanabe J, M Thamilarasan, E H Blackstone, J D Thomas, M S Lauer. Heart rate recovery immediately after treadmill exercise and left ventricular systolic dysfunction as predictors of mortality: The case of stress echocardiography. *Circulation,* 2001; 104:1911-1916.
(b) 23±8; N=2097
Reference:
Deepak P. Vivekananthan, Eugene H. Blackstone, Claire E. Pothier Snader, and Michael S. Lauer. Heart rate Recovery After Exercise Is a predictor of Mortality, Independent of the Angiographic Severity of Coronary Disease. J Am Coll Cardiology; 2003: 42:831-838.
Mean Normal Value=28±8.
Cut-Off Values for HF:
(a) < or =12; N=838
Reference:
Deepak P. Vivekananthan, Eugene H. Blackstone, Claire E. Pothier Snader, and Michael S. Lauer. Heart rate Recovery After Exercise Is a predictor of Mortality, Independent of the Angiographic Severity of Coronary Disease. J Am Coll Cardiology; 2003: 42:831-838.
4. CRI or Chronotropic Response Index
Normal Values:
(a) 0.94±0.16; N=470
Reference:
Robbins M, G Francis, F J Pashkow, C E Snaker, K Hoercher, J B Young, M S Lauer. Ventilatory and heart rate responses to exercise: better predictors of heart failure mortality than peak oxygen consumption. *Circulation,* 1999; 100:2411-2417.
(b) 0.93±0.15; N=323
Reference:
Dresing T J, E H Blackstone, F J Pashkow, C E Snader, T H Marwick, S L Lauer. Usefulness of impaired chronotropic response to exercise as a predictor of mortality, independent of the severity of coronary artery disease. *Am J Cardiol,* 2000; 86:602-609.
Cut-Off Values:
(a) HF patients: CRI=</=0.51
Reference:
Robbins M, G Francis, F J Pashkow, C E Snaker, K Hoercher, J B Young, M S Lauer. Ventilatory and heart rate responses to exercise: better predictors of heart failure mortality than peak oxygen consumption. *Circulation,* 1999; 100:2411-2417.
(b) Mild to severe/CAD: CRI</=0.8
Reference:
Dresing T J, E H Blackstone, F J Pashkow, C E Snader, T H Marwick, S L Lauer. Usefulness of impaired chronotropic response to exercise as a predictor of mortality, independent of the severity of coronary artery disease. *Am J Cardiol,* 2000; 86:602-609.

The invention claimed is:

1. A method of pattern recognition for classifying and evaluating the functional status of a patient with chronic disease comprising:
   determining a plurality of individual variable indexes (IVIs), wherein the value for each IVI is calculated, in part, from cardiopulmonary exercise test measurements gathered from sub-maximal exercise bouts, and wherein the exercise test measurements include Resting $PetCO_2$, $\Delta PetCO_2$, $SaO_2$, OUES, $V_e/VCO_2$ slope, and a non-invasive estimate of pulmonary capacitance equal to $O_2$pulse×Pet $CO_2$;
   determining a plurality of weighted IVIs by multiplying each IVI by a weighting value for that IVI;
   calculating, by a computer system, a multivariable index score (MVI), wherein the MVI is the result of dividing the sum of the plurality of weighted IVIs by the sum of the weighting values for each IVI;
   classifying said functional status based on the MVI.

2. A method as in claim 1 wherein each IVI is given a weighted value of <1.00 to about 4.00, the weighted value increasing relative to the IVI's relation to disease severity.

3. A method as in claim 1 wherein one or more of the IVIs are weighted by a value other than 1.00.

4. A method as in claim 1 wherein the value of one or more IVIs is weighted using a value >1.00.

5. A method as in claim 1 wherein the MVI is increased for a negative slope of change and magnitude of change in $PetCO_2$ during exercise.

6. A method as in claim 1 wherein the plurality of IVIs includes an IVI based on the equation:

$$IVI=((1+(V_e/VCO_2\text{slope}NV-\text{Measured})/V_e/VCO_2\text{slope}D))*-1)+1.$$

7. A method as in claim 1 wherein the plurality of IVIs includes an IVI based on the equation:

$$IVI=((1+((\text{Measured}-OUESNV)/OUESD))*-1)+1.$$

8. A method as in claim 1 wherein said multivariable index (MVI) is a continuous variable in the range of <1.00 to about 4.00.

9. A method as in claim 1 wherein the value of one or more IVIs is weighted using a value of 1.00.

10. A method as in claim 1 wherein the value of one or more IVIs is weighted using a value <1.00.

11. A method as in claim 1 wherein the value of all IV's is weighted using a value of 1.00.

12. A method as in claim 1 wherein the plurality of IVIs includes an IVI based on the equation:

$$IVI=((1+((\text{RestingPetCO}_2\text{Measured}-\text{RestingPetCO}_2NV)/\text{RestingPetCO}_2D)*-1)+1.$$

13. A method as in claim 1 wherein the plurality of IVIs includes an IVI based on the equation:

$$IVI=((1+((\Delta PetCO_2\text{Measured}-\Delta PetCO_2NV)/\Delta PetCO_2D)*-1)+1.$$

14. A method as in claim 1 wherein the plurality of IVIs includes an IVI based on the equation:

$$IVI=((1+((SaO_2\text{Measured}-SaO_2NV)/SaO_2D)*-1)+1.$$

15. A method as in claim 1 wherein the plurality of IVIs includes an IVI based on the equation:

$$IVI=((1+((P_{CAP}\text{Measured}-P_{CAP}NV)/P_{CAP}D)*-1)+1.$$

16. A method of pattern recognition for classifying and evaluating the functional status of a patient with chronic disease comprising:
   determining a plurality of individual variable indexes (IVIs), wherein the value for each IVI is calculated, in part, from cardiopulmonary exercise test measurements gathered from sub-maximal exercise bouts, and wherein the exercise test measurements include Resting $PetCO_2$, $\Delta PetCO_2$, $SaO_2$, OUES, $V_e/VCO_2$ slope, and a non-invasive estimate of pulmonary capacitance equal to $O_2$pulse×Pet $CO_2$;
   calculating, by a computer system, a multivariable index score (MVI), wherein the MVI is the sum of the plurality of IVIs; and
   classifying said functional status based on the MVI.

17. A method of pattern recognition for classifying and evaluating the functional status of a patient with chronic disease comprising:
   determining a plurality of individual variable indexes (IVIs), wherein the value for each IVI is calculated, in part, from cardiopulmonary exercise test measurements gathered from sub-maximal exercise bouts, wherein the plurality of IVIs includes an IVI based on [((1+((RestingPetCO$_2$Measured-RestingPetCO$_2$NV)/RestingPetCO$_2$D)*-1)+1], wherein the plurality of IVIs includes an IVI based on [((1+((-$\Delta PetCO_2$Measured-$\Delta PetCO_2$NV)/$\Delta PetCO_2$D)*-1)+1], wherein the plurality of IVIs includes an IVI based on [((1+((SaO$_2$Measured-SaO$_2$NV)/SaO$_2$D)*-1)+1], wherein the plurality of IVIs includes an IVI based on [((1+((OUESMeasured-OUESNV)/OUESD))*-1)+1], and wherein the plurality of IVIs includes an IVI based on [((1+((V$_E$VCO$_2$slopeNV-V$_E$VCO$_2$slopeMeasured)/V$_e$VCO$_2$slopeD))*-1)+1];
   calculating, by a computer system, a multivariable index score (MVI), wherein the MVI is the sum of the plurality of IVI's; and
   classifying said functional status based on the MVI.

18. A method as in claim 17 wherein the plurality of IVIs includes an IVI based on a non-invasive estimate of pulmonary capacitance equal to $O_2$pulse×Pet $CO_2$.

* * * * *